United States Patent
Schroeder et al.

[11] Patent Number: 5,140,985
[45] Date of Patent: Aug. 25, 1992

[54] NONINVASIVE BLOOD GLUCOSE MEASURING DEVICE

[76] Inventors: Jon M. Schroeder, 14301 Bagdad Rd., Leander, Tex. 78641; Joseph F. Long, 1335 Lost Creek Rd., Austin, Tex. 78746

[21] Appl. No.: 781,485

[22] Filed: Oct. 21, 1991

Related U.S. Application Data

[63] Continuation-in-part of Ser. No. 738,861, Aug. 1, 1991, which is a continuation of Ser. No. 448,249, Dec. 11, 1989, abandoned.

[51] Int. Cl.⁵ .............................................. A61B 5/00
[52] U.S. Cl. ................................. 128/632; 128/635
[58] Field of Search ....................... 128/632, 635, 637

[56] References Cited

U.S. PATENT DOCUMENTS 5,050,604  9/1991  Reshef et al. .................. 128/635

Primary Examiner—Kyle L. Howell
Assistant Examiner—Robert L. Nasser, Jr.
Attorney, Agent, or Firm—Joseph F. Long

[57] ABSTRACT

This invention gives an indication of blood glucose by measuring the glucose content in sweat. Other bodily fluids such as saliva, urine, or tears could also be used. The measuring system in our unit includes the substrate which may have printed wiring thereon; a plurality of oxygen sensors for measuring oxygen remaining after oxidation of the glucose with glucose oxidase and a reference oxygen sensor, all covered by a semi-porous membrane; a wick for conveying sweat to the glucose sensors and beyond; a battery, and a plurality of electroplateable indicator bars for indicating the glucose concentration in the sweat by difference in electrical output between the reference oxygen sensor and oxygen sensors that measure oxygen after reaction with the glucose oxidase or glucose sensors; a calibrateable legend associated with the bars relates the plating to the glucose level in the blood. In a second embodiment a liquid crystal display replaces the electroplateable indicator bars. This assembly allows the measurement of glucose level as related to glucose found in sweat by directly attaching the device to the arm and priming or activating the device with an electrolyte after which the measuring device will react with localized sweating and indicate the wearer's blood glucose level for at least an 18 hour period. The sealed monolithic unit becomes the entire measuring instrument and indicating device.

10 Claims, 4 Drawing Sheets

NONINVASIVE BLOOD GLUCOSE MEASURING DEVICE

BACKGROUND

This is a continuation-in-part of my patent, Ser. No. 07/738,861, filed Aug. 8, 1991, which is a continuation of my patent Ser. No. 07/448,249, filed Dec. 12, 1989 now abandoned entitled "A Noninvasive Blood Glucose Measuring Device."

There are 11 million known diabetics in the United States. It is estimated that another 20 million people are predisposed to this disease while as many as 10 million diabetics may remain undiagnosed. Diabetes is a relentless disease, constantly degrading the person's health. Obesity is considered a major contributor to the disease rather than a symptom of it. Insulin from the body normally controls the level of blood sugar. However, in type 2 diabetes, the body's insulin is not effective and blood sugar levels rise too high. Complications of this effect can include kidney disease, blindness, and gangrene, which can require leg and foot amputations. Type 2 diabetes afflicts the vast majority of the nation's diabetics, according to the American Diabetes Association. The disease can often be controlled by diet and exercise only. This invention opens the door to more desirable and much closer control by the affected individual as well as easier scientific study of the disease at a level that hasn't been possible.

It has been said that no one ever dies of diabetes. It is common knowledge, however, that these persons live short lives with a multitude of health complications. Because control of this disease is an hour by hour health control problem for the diabetic, they must be made an informed partner in the maintenance of their health. This means that control of the disease is the primary responsibility of the diabetic patient with minimal supervision by health care specialists.

A major problem in treating one's own diabetes, is predicting accurately blood glucose level at different times of the day. An estimate is usually made, based on the results of a painful finger prick and blood tests, performed early each morning. The theory says that diet, exercise, and medication can each be juggled to accommodate the activities of a varying day based upon the daily test. Urine tape and tablet test methods for determining blood glucose are also on the market; however, these tests can be misleading if not performed frequently and require the privacy of a restroom. The prick test before morning insulin injection does not predict glucose level performance during the day and tests must be repeated often to obtain close blood sugar measurements. The pin prick test is painful, and so annoying that the information that a patient needs to properly control the disease may not be taken by the patient. The individual is then placed at higher risk to the ravages of the disease. Considering these various deficiencies in present blood glucose determination methods, a process is needed that measures glucose in a convenient manner in an easily obtained body fluid on a continuous basis to provide an indication of glucose concentration in the blood for the person wearing the device.

Briefly, in one preferred embodiment of the present invention, the proposed device will be an adhesive type patch appliance, consisting of a tick film battery, sensors for measuring glucose level in sweat or saliva, and indicators that present a visual bar chart of the wearer's blood sugar.

This invention covers the need to simultaneously measure and indicate glucose concentration in the blood on a continuous basis to allow a diabetic person to be aware of the glucose level in their blood or the control achieved over the disease at any time of the day. With continuous knowledge of blood glucose levels, modifications can be made by the patient as to diet, exercise, or antidiabetes medication, to control and greatly delay the consequences of the disease.

This patent relates to a noninvasive sensing, measuring, and indicating device for blood glucose measurement. The device produces real-time indication of the glucose concentration in sweat, this concentration has been found to be approximately 1% of the glucose level in the blood. The device allows enzymatic and electrochemical reactions to occur uniformly with a sweatmoving wick operating to move sweat past a sensing device. Glucose level is quantified with a bridge system that compares oxygen in sweat with residual oxygen in sweat after a portion of sweat reacts with a glucose oxidizing enzyme. The system is comprised of electronic circuitry with a battery, sensors and a reference sensor, and electrochemical indicator and a sweatmoving wick. In one embodiment, the system or unit operates to automatically indicate ascending and descending glucose levels over the course of a day by virtue of plating action to cause visible bars to change color. This embodiment covers a low cost, disposable unit that will result in a body worn, direct reading glucose meter as an alternative to other more bothersome blood sugar tests.

An advantage of the present invention is that it provides a more desireable method for the wearer to quickly check and correct a low blood glucose condition with the ingestion of candy, before the onset of unconsciousness or diabetic coma. Additional benefit to emergency health care specialists when responding to a comatized patient wearing the device, will be realized by their understanding of the condition of the patient by the visual read out on the unit.

Still another advantage of the present invention will be the potential to improve the health of 4% of this nation's populations (diabetics); providing them with more information for the control of this disease will equate to lower health maintenance costs. The device may also provide an effective method of public screening for diabetics by handing out the devices free of charge to detect the disease at earlier stages when treatment and control is more effective.

Another advantage of the present invention is to provide a more desireable method of determining blood glucose without the requirement of drawing blood. However, the method of drawing blood may be used to calibrate the body worn display instrument from time to time.

Still another feature of the present development is to provide an assembly for connecting a number of sensors and continuous indicators as a packaged electronic circuit in such a manner that the total assembly occupies a small area on the skin or body of the person.

Another feature of the present invention is to provide a sealed conducting means or capillary means to move sweat from the body, past the sensors for blood glucose level determination and on to be evaporated regardless of the glucose concentration in the sweat of the person wearing the device.

Another feature of the present invention is to provide a method of constantly determining blood glucose so that by anti-diabetes medication, diet, and exercise, a person wearing the device can keep blood glucose within the levels safe for health.

Still another feature of the present development is to provide a manufacturing method that will allow automation and production of a measuring device that otherwise requires time consuming, costly, manual methods of determination of blood glucose level. Presently, much of the blood glucose analysis is deferred by the patient because of inconvenience and cost with a resulting decrease in the diabetic's health.

Briefly, these and other features and advantages are accomplished in one preferred embodiment of the present development by an assembly which includes a conductive ciruit drawn or printed on a preform, glucose sensors, a reference sensor, a wick that acts as a sweat pump and a battery; all in a form designed to have an operating life of 18 hours or more after activation, producing measurement and indication of blood glucose levels consistent with that obtained by blood samples.

T. C. Boysen, Shigeree Yanagaun, Fusaho Sato and Uingo Sato in a paper published in 1984 in the Journal of Applied Psychology described a modified method for sweat collection and in this paper they also showed that two different people each had a glucose concentration in blood plasma of about 100 mg/dl or 1000 ppm before ingestion of a large amount of glucose. Subject A had approximately 1 ppm glucose in his perspiration while the other, subject B, had approximately 6 ppm glucose in his perspiration. After ingestion of glucose, both A and B had approximately 3500 ppm glucose in the blood plasma but in less than 5 minutes, glucose in the blood plasma of B had dropped to approximately 3000 ppm, while glucose in blood plasma of A had dropped to less than 2000 ppm. At the same time, glucose in perspiration from subject B rose to over 10 ppm and glucose in perspiration from subject A rose to over 3 ppm.

This data indicates that our device to measure glucose in perspiration must be calibrated for each person. The data also indicates a correlation between changes in glucose in blood plasma and glucose in perspiration. Thus a user of the invention would calibrate the output signal against the usual blood measurement of glucose.

There are several embodiments of the invention that will be more fully described in the following pages.

SUMMARY OF THE INVENTION

The basic purpose of the invention is to determine glucose in the blood with sufficient accuracy on a continuous basis to allow a diabetic person to control the disease with diet, exercise, use of insulin, etc. In a preferred embodiment, electronic circuitry comprising an oxygen measuring reference cell, one or more other oxygen measuring cells in glucose sensors, also called glucose sensing units, wherein sweat is first reacted with glucose oxidase and visable read-out by plating on a series of strips to indicate the difference of oxygen content in sweat when a portion treated with glucose oxidase is compared with an untreated portion. This electronic circuitry is printed on a plastic strip that may be approximately 1 inch wide and 3 inches long and is powered by a chemical type battery that may be less than ⅛ thick and is located on the same strip. Perspiration is moved past and contacts the oxygen measuring cells in the glucose sensor units and an oxygen measuring reference cell using a wick that then leads to the air so that evaporation and capillary actions moves the perspiration.

In a preferred embodiment a strip containing the circuitry and wick as described fits into a insulating cover that may be held around a portion of the body to keep the wick in close contact with the skin using a fastener such as Velcro. The insulation serves to stimulate sweat production and to provide a body temperature environment for proper operation of the oxygen reference cell, enzymatic oxidation of the glucose, and operation of glucose sensors.

DETAILED DESCRIPTION OF THE INVENTION

The assembly may be briefly described as follows:
a. a substrate with electronic circuitry including an oxygen reference cell, glucose sensors, chemical battery and plateable glucose indicator strips;
b. an insulating spacer placed and sealed on the substrate;
c. a fibrous wick material placed in the assembly to collect and transfer body sweat to the reference cell and to the glucose sensing elements or glucose sensors and out to the atmosphere for evaporation;
d. Means to insulate and hold the wick in the assembly close to the skin for operation;
e. means of applying electrolyte or water (such as eye dropper to drop liquid through an aperture) to the internal battery of the unit to cause chemical operation and sustained voltage;
f. means to apply water to fibrous wick material to speed up initial operation;

In one preferred embodiment the assembly is more specifically described in the following paragraphs.

Figure 1:
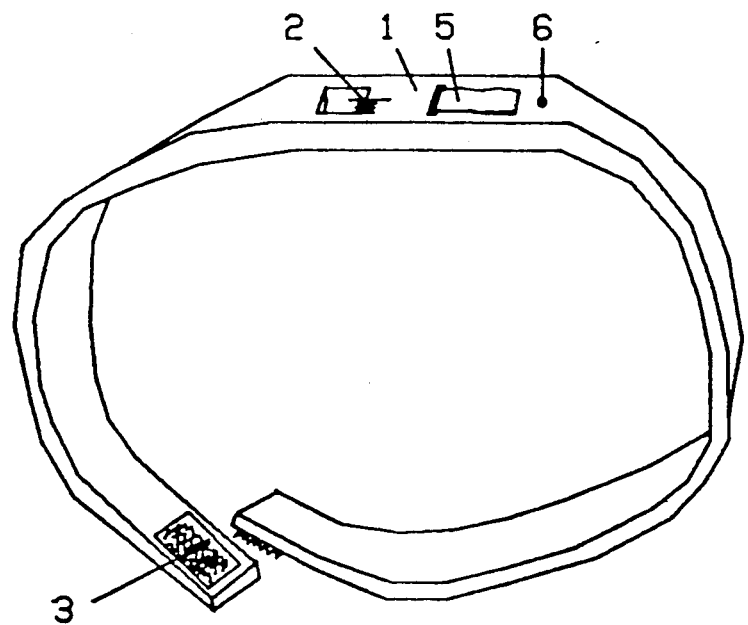
In FIG. 1 we show an assembly top view of one embodiment of the unit designed to use a replaceable strip containing the sweat-moving wick, fixed glucose oxidase over the glucose sensors and plateable strip read out.

In FIG. 1 we show a view of one preferred embodiment designed to fit around an arm. Any body location wherein sweat is generated would be usable for other embodiments. A thick insulating band 1 holds a replaceable strip 7, FIG. 2. A wick 5 is used with strip 7, FIG. 2, and extends through insulating band 1 for evaporation. A Velcro fastener 3 is used to fasten the band to the body. The opening 6 allows adding water to activate a chemical battery 9, FIG. 3.

Figure 2:
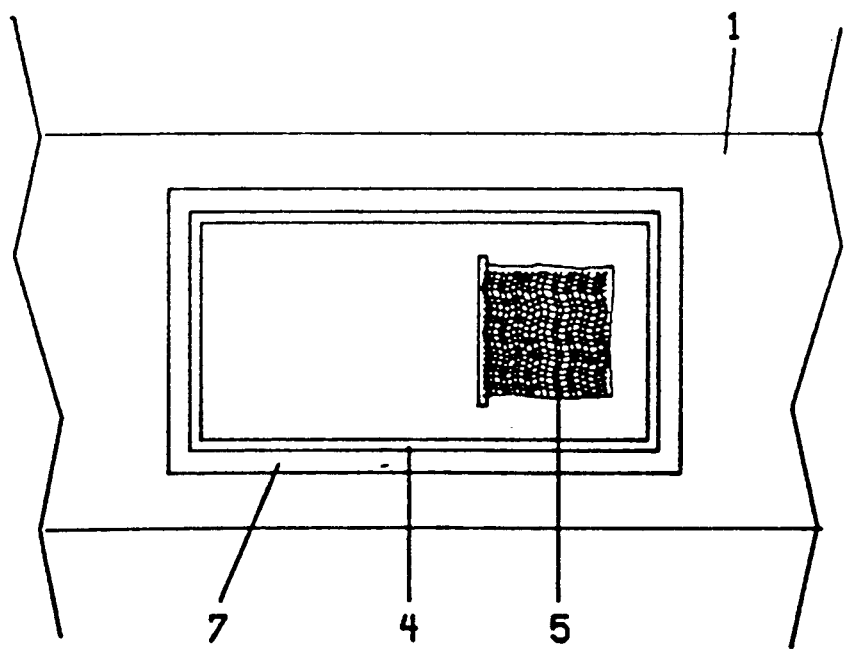
In FIG. 2 we show the underside of the top portion of the FIG. 1 assembly indicating a soft sealing ring 4 and the underside of wick 5. The sealing ring allows the unit to fit closely to the skin.

In FIG. 2 we show the underside of the insulating band 1 which may have a depression to fit replaceable strip 7 and has a soft raised plastic sealing ring 4 to completely seal in the wick 5 on the underside. The sealing plus insulation plus some heat from a battery 9, FIG. 3, serves to generate sweat which moves through the wick 5, FIG. 3, by evaporation. On the average, each person perspires about one pint per day.

Figure 3:
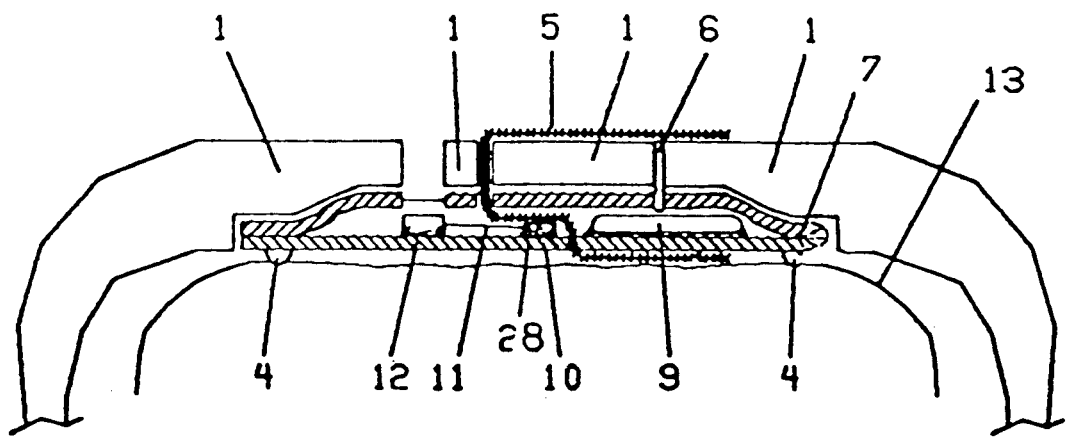
In FIG. 3 we show a view of a part of assembly 1 showing some details of the replaceable, strip containing all the working elements of the invention held in place by the insulating hold down strap.

In FIG. 3 we show a cross section of a replaceable detector-measuring strip 7 also called a replaceable strip that fits into the underside of insulating band 1. The insulating band 1 serves to hold the replaceable strip 7 closely against the skin 13 with soft sealing ring 4 making a seal. Replaceable strip 7 has sealing ring 4 formed on an underside of the strip and on the top side above the sealing ring area are formed plateable electrodes 12, sensing elements 10, an oxygen reference cell 28 and battery 9 with connecting circuitry 11. Between battery 9 and sensors 10 an opening allows wick 5 to be placed between battery 9 and sensors 10 and, after strip 9 is folded over as shown in FIG. 3, wick 5 contacts sensors 10 and oxygen reference cell 28 and feeds through a second opening in strip 7 and through the insulating band holder 1. The total strip, which is folded approximately at the mid point, is contained in a cavity in insulating band 1. This embodiment uses battery 9 heat, insulation in insulating band 1 and sealing by the soft sealing ring 4 to generate perspiration and to maintain glucose sensors 10 and oxygen reference cell 28 at essentially a constant body temperature. The wick 5 moves perspiration or sweat past sensors 10 and 28. This allows optimum operation of the sensors that in turn comprise an oxygen reference cell and glucose sensor units that are set up to measure oxygen in the perspiration after the perspiration is contacted with glucose oxidase causing the oxygen in the perspiration to react with glucose in the perspiration or sweat. The difference in oxygen between the reference cell and the glucose sensor units is proportional to the glucose present in the perspiration. The electronic circuitry as shown in FIG. 6 measures and indicates this difference. With minor circuitry changes the Hydrogen proxide produced, which is also indicative of the amount of glucose, could be used. We have shown the sweat carrying wick 5 going well past the glucose sensors 10 to prevent back diffusion of oxygen to the sensors. With minor changes we could provide oxygen saturation and measure hydrogen peroxide formed in glucose sensors 10, FIG. 5, versus that formed, which should be zero, in the oxygen reference cell 28, FIG. 4.

Figure 4:
FIG. 4 shows a cross-section of the oxygen reference cell.

In FIG. 4 we show a side view of an oxygen reference cell 28 wherein an anode 23 is surrounded by a semi-circular cathode 21 with electrolyte 23 sealed below an oxygen permeable membrane 24. The anode, cathode, and connecting wiring are drawn with a computer CAD system using conductive inks of proper composition.

Figure 5:
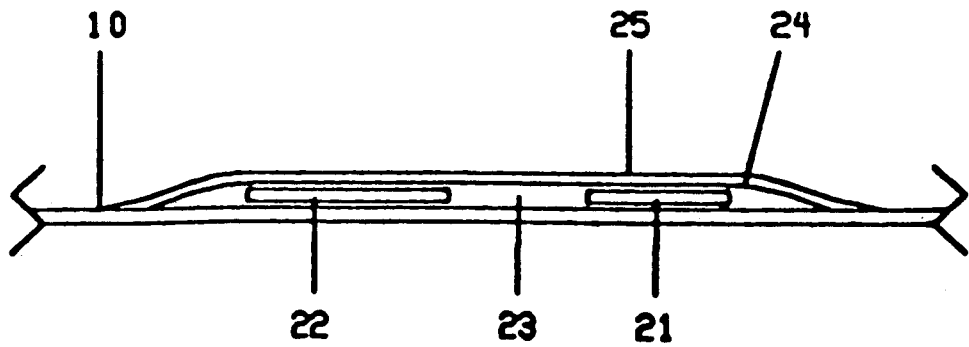
FIG. 5 shows a cross section of the glucose sensing units or glucose sensor which differ from reference cell 28, FIG. 4, in that the sweat contacts glucose oxidase wherein oxygen from the sweat reacts with any glucose to use up part of the oxygen with the remainder diffusing to the electrodes of the cell.
Figure 6:
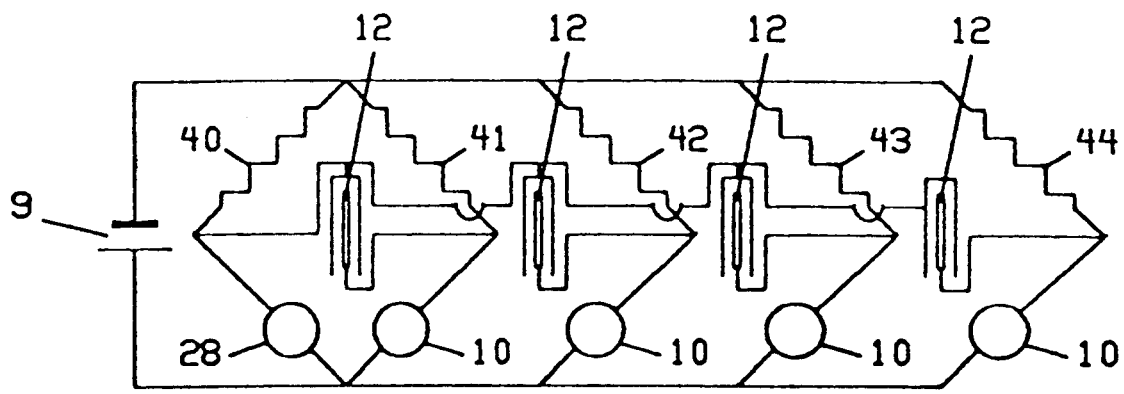
FIG. 6 shows the circuitry to indicate glucose concentration using plateable electrodes.

In FIG. 5 we show a glucose sensor 10, shown in detail in FIG. 3, that differs from the oxygen reference cell 28, FIG. 4 in that a permeable sheet 25 with glucose oxidase chemically affixed thereto maybe affixed over the semi-permeable membrane 24 so that the perspiration or sweat containing glucose (when glucose is present) first contacts the glucose oxidase using up oxygen to react with glucose present. Past studies indicate that there is sufficient oxygen present for the system to react in this way. As outlined, we could change to peroxide measure as an alternative approach.

In FIG. 6 we show a modified Wheatstone bridge circuit to compare output of the glucose sensors 10 against the oxygen reference cell 28. The system is powered by a battery 9 that may be conveniently made by sealing a dry chemical, such as citric acid, between two printed electrodes with provisions for adding a few drops of water for activation of the battery. Other type batteries to produce about 1.5 volts for our preferred embodiment would also be useable. We prefer the 1.5 volts because in our circuit this gives the necessary 0.7 volts across the oxygen measuring cells so that plateable carbon electrodes 12 will plate from a stannous chloride electrolyte to make a visible strip as each plateable carbon electrode is plated. Looking at the first segment the resistors 40 and 41 can be chosen to cause plating of the first electrode 12 with a minimum output difference between reference cell 28 and the first glucose sensor 10. Looking further the resistor 42 may be chosen so that a different output between reference cell 28 and the second sensor 10 causes plating of the second plateable electrode 12. In the same way resistors 43 and 44 may be chosen so that we have four levels of glucose in sweat with each indicated by the location of the electrode that is plating. Obviously more glucose sensors could be added to measure glucose more exactly. Each user will need to calibrate the plating on strips 10 with glucose in the blood determined by the usual pin-prick method; this is done by marking the electrode that is plated to a silver color adjacent to an unplated carbon electrode with the amount of glucose determined by the usua pin prick method. The battery and glucose oxidase as we have described should have a minimum life of more than 18 hours so that use of one replaceable strip 7 per day should give essentially continuous monitoring. Operation of the total unit may also be described as follows: After activating battery 9 by addition of water as previously indicated, the Wheatstone Bridge modified circuitry we show operates the same as if we had separate multiple Wheatstone Bridges. Consider the first section of FIG. 6 wherein we have a typical Wheatstone Bridge formed with oxygen reference cell 28 and oxygen measuring cell of glucose sensing unit 10 in two legs of the bridge with resistors 40 and 41 in upper legs. If 28 and 10 were resistors and resistors 40 and 41 were the resistors of the same resistance as 28 and 10, no current would flow through stannous chloride electrolyte 14 to plate electrode 12. In a normal oxygen measuring cell shown in FIG. 4, oxygen diffuses through semi-permeable membrane 24 to electrolyte 23 and with impressed current from the battery, oxygen reacts to form hydrogen peroxide with a current flow as is known in the art. For ease of understanding the reference cell 28 acts as though it were a resistor of one value dependent upon amount of oxygen diffusing therein but will be essentially constant as oxygen in perspiration is known to be essentially constant. Now cell 10 also acts as though it were a resistor of differing values dependent upon the amount of oxygen left after glucose reacts with the glucose oxidase. Now resistors 40 and 41 can be chosen to have no plating of electrode 12 when no glucose is present in perspiration and the oxygen being measured in cell 10 is the same as being formed in cell 28. Now if glucose were present oxygen being measured in cell 10 would change according to glucose present and one of electrodes 12 would plate. By changing size of resistors 41, 42, 43 and 44 as the amount of glucose changes and the particular ones of electrodes 12 that plate changes accordingly. A user then calibrates the unit by marking the position of the plated electrode 12 next to the unplated electrode with amount of glucose determined by conventional methods such as the pin-prick method. A diabetic user would calibrate the unit by determining his blood glucose when he know the blood glucose is low and mark the electrode that is plated with the number determined. He then ingests a relatively large amount of glucose such as in candy and tests again and marks a second electrode that plates. His glucose variation can be read thereafter by determining location of the plated electrodes to indicate glucose present in the bloodstream. The circuitry and unit as described with changes in electrodes and enzymes should be useful to measure other components of bodily fluids as well as measuring glucose.

Figure 7:
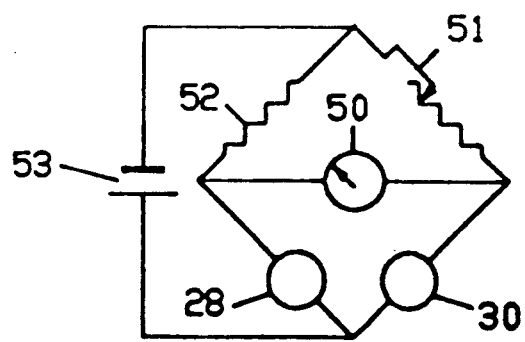
FIG. 7 shows alternative circuitry wherein a polarographic glucose measuring cell is used with a Wheatstone bridge Null-point ammeter sensor.

In FIG. 7 we show the circuitry for another embodiment that could be used in the same insulating band 1 and either with a chemical battery or one of a number of small dry cell batteries 53 in a Wheatstone bridge type circuit with an oxygen reference cell 28, a glucose sensor 10 that may be larger than other glucose sensors 10, FIG. 6, with a fixed resistor 52 and variable resistor 51 to zero a null point ammeter 50. The position of the variable resistor 51 would be calibrated by the user in the usual way in terms of glucose in the blood. Calibrateable automatic circuitry to continuously zero the null point ammeter would also be within the scope of this embodiment.

Figure 8:
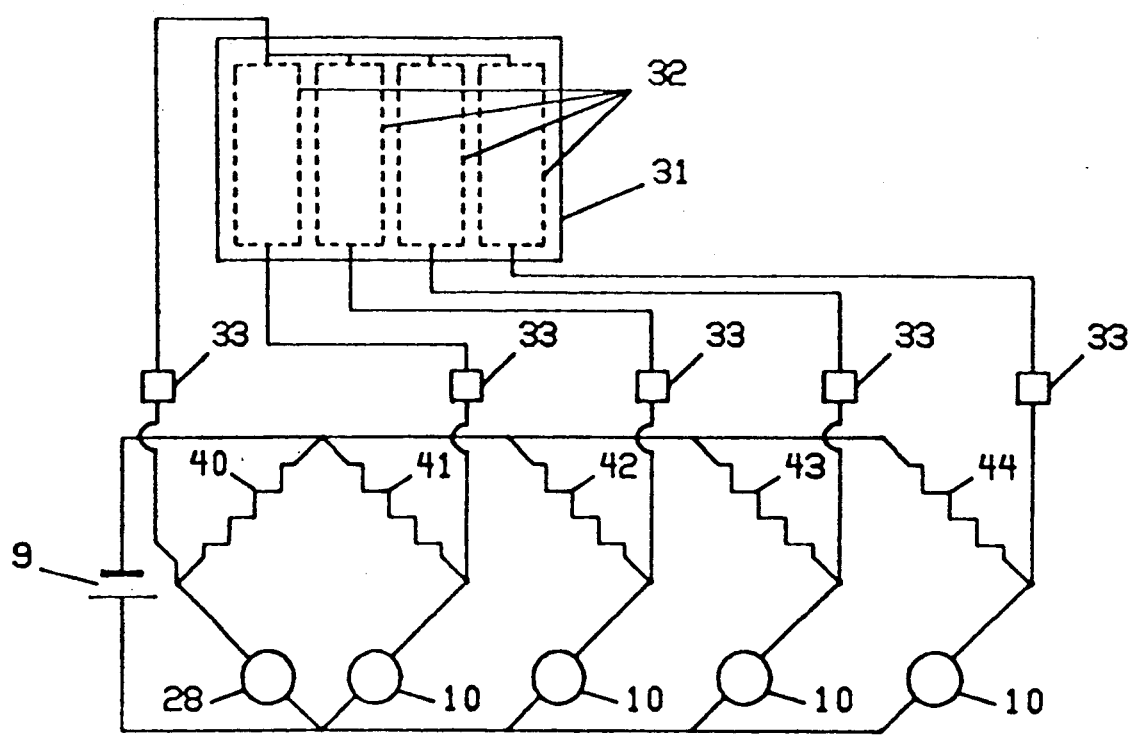
FIG. 8 shows alternative circuitry with a liquid crystal display for displaying the glucose levels.
Figure 9:
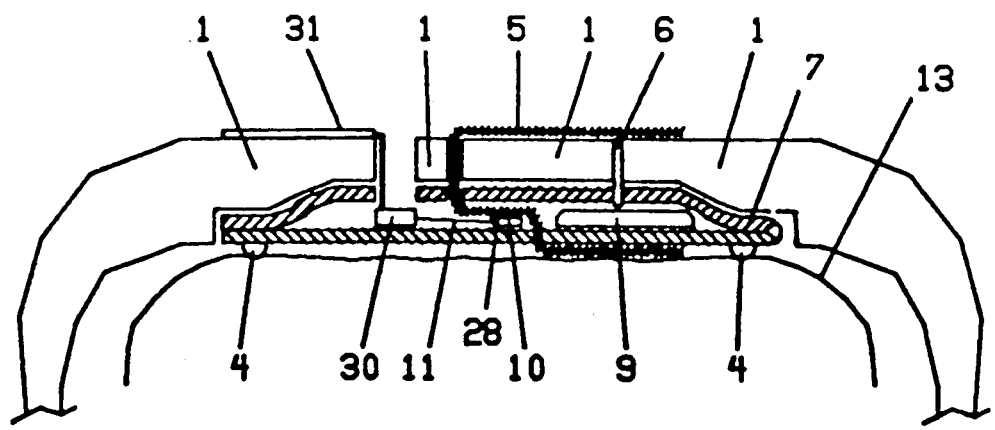
FIG. 9 shows an alternative embodiment of FIG. 3 which uses the display shown in FIG. 8.

In FIG. 8 we show circuitry for another embodiment wherein plateable strips 12 on replaceable strip 7, FIG. 3, is replaced with contact nodes 33 that make contact with leads to a liquid crystal display unit 31 that may be mounted on a topside of insulating bandholder 1, as shown in FIG. 9. Preferably the liquid crystal display is in the form of bars 32 with location of the bar indicating amount of glucose present.

FIG. 9 is essentially the same as FIG. 3 but differs in having contact nodes 33 leading to a liquid crystal display unit 31 with location of the bars 32, FIG. 8 indicating glucose concentration. The user must calibrate the bars by using an independent glucose measuring method such as the pin prick method in the same way as outlined for plateable strips 12, FIG. 6.

Many modifications to the oxygen measuring cells and the glucose sensor units in electrolyte, electrode shape, etc. may be made by one of normal skill in electronic and biochemical art so we wish only to be limited by the spirit and purpose as outlined in these claims and specifications.

LEGEND

FIG. 1
1 = insulating band holder
2 = detection meter
3 = Velcro fastener
5 = wick
6 = opening to add water to the battery
FIG. 2
1 = insulating band holder
4 = soft plastic seal ring
5 = wick
7 = replaceable strip
FIG. 3
5 = wick
7 = replaceable strip
9 = battery
10 = sensing elements
11 = electronic circuitry
12 = plateable electrodes
13 = skin
14 = insulating band holder
15 = spacer strips
16 = cover strip
FIG. 4
21 = anode
22 = cathode
23 = gel-type electrolyte
24 = semi-permeable membrane
28 = oxygen reference cell
FIG. 5
10 = glucose sensing elements
21 = cathode
22 = anode
23 = gel-type electrolyte
24 = oxygen permeable membrane
25 = fixed glucose oxidase
FIG. 6
9 = battery
10 = glucose sensor
12 = plateable electrode—carbon in stannous chloride
14 = electrolyte such as stannous chloride
28 = oxygen reference cell
40 = resistor
41 = resistor
42 = resistor
43 = resistor
44 = resistor
FIG. 7
28 = reference sensor
30 = glucose sensor
50 = ammeter
51 = calibrated variable externally operated resistor
52 = fixed resistor
53 = battery
FIG. 8
9 = battery
10 = glucose sensor
28 = oxygen reference cell
31 = liquid crystal display unit
32 = bars that light up
33 = contact nodes
40 = resistor
41 = resistor
42 = resistor
43 = resistor
44 = resistor
FIG. 9
5 = wick
7 = replaceable strip
9 = battery
10 = sensing elements
11 = electronic circuitry
13 = skin
14 = insulating band holder
15 = spacer strips
16 = cover strip
31 = liquid crystal display unit 33 = contact nodes

What is claimed is:

1. A non-invasive glucose monitoring unit comprising:
   a. a housing means;
   b. a replaceable strip means with a sealing ring to seal against a persons skin in said housing means;
   c. an oxygen reference cell and multiple glucose sensing units on said replaceable strip means;
   d. a wick means in said housing means whereby clean perspiration is picked up from skin by said wick means and transported past said oxygen reference cell and past said multiple glucose sensing units both of which are integrally formed on said replaceable strip means;
   e. a glucose oxidizing enzyme contained in each of said multiple glucose sensing units;
   f. an oxygen measuring cell in each of said multiple glucose sensing units;
   g. an electronic circuitry means formed on said replaceable strip means in said housing means to measure and indicate difference in oxygen in each of said multiple glucose sensing units compared with oxygen present in said oxygen reference cell;
   h. a battery means in said housing means to power said electronic circuitry means.

2. A non-invasive glucose monitoring unit as in claim 1 wherein said electronic circuitry means comprises a group of electrodes each immersed in a plateable solution with each one of said group of electrodes connected with circuitry to compare the difference in electrical output between said oxygen reference cell and said oxygen measuring cell in each of said glucose sensing units; said electronic circuitry means having a different sized resistor cooperating with each of said oxygen measuring cells thereby plating a different one of said electrodes for different levels of said electrical output between said oxygen reference cell and one of said oxygen measuring cells.

3. A non-invasive glucose monitoring unit as in claim 2 wherein said group of electrodes each comprises a carbon electrode in a stannous chloride electrolyte with the silver color of the plated carbon electrode being the indicating means whereby the difference in output between said oxygen reference cell and each of said oxygen measuring cells in said multiple glucose sensing units are visually indicated.

4. A non-invasive glucose monitoring unit as in claim 1 wherein said battery means is a chemical battery formed on said replaceable strip.

5. A non-invasive glucose monitoring unit as in claim 1 wherein said wick means is a wick that leads from under said replaceable strip means, through said replaceable strip means and over said oxygen reference cell and said multiple glucose sensing units and out through said housing means for evaporation of said perspiration.

6. A non-invasive glucose monitoring unit as in claim 5 wherein said housing means has a insulating portion and an interclasping fastener to hold said replaceable strip means close to an individual's skin thereby promoting formation of perspiration and minimizing ambient oxygen diffusion to perspiration in said wick.

7. A non-invasive glucose monitoring unit comprising:
   a. a housing means with flexible means to hold said housing means in contact with skin;
   b. a battery in said housing means;
   c. a replaceable strip means and a sealing ring means for said replaceable strip means in said housing;
   d. an oxygen reference cell and a glucose sensing unit, said glucose sensing unit comprising an oxygen measuring cell and a glucose oxidizing enzyme;
   e. a wick means in said housing means whereby clean perspiration may be picked up from the skin and hermetically transported past said oxygen reference cell and means whereby a portion of said clean perspiration may be hermetically transported past said glucose sensing unit with means for contacting said portion of said clean perspiration with said glucose oxidizing enzyme in said glucose sensing unit;
   f. a Wheatstone Bridge circuit means in said housing means and powered by said battery in said housing means wherein an output from said oxygen measuring cell in said glucose sensing unit is compared with said oxygen reference cell with a position of a variable resistor used to zero a null point ammeter indicating glucose concentration in said clean perspiration.

8. A non-invasive glucose monitoring unit comprising:
   a. a housing means;
   b. a replaceable strip means contained in said housing means;
   c. a sealing ring on said replaceable strip means allowing said housing means to seal said replaceable strip means to a person's skin;
   d. an oxygen reference cell and multiple glucose sensing units formed on said replaceable strip means;
   e. a wick means to collect and hermetically transport perspiration to contact said oxygen reference cell and said multiple glucose sensing units; said wick means extending through said housing means allowing evaporation and capillary action to cause said perspiration transport;
   f. an oxygen measuring cell, an oxygen permeable membrane and fixed glucose oxidase comprising each of said multiple glucose sensing units;
   g. a battery means in said housing means;
   h. an indicator means visible through said housing means and electronic circuitry means powered by said battery means and cooperating with said oxygen reference cell, said multiple glucose sensing units, and said indicator means to indicate glucose concentration by difference in output between said oxygen reference cell and said multiple glucose sensing units.

9. A non-invasive glucose monitoring unit as in claim 8 wherein said indicator means is a liquid crystal display unit.

10. A non-invasive glucose monitoring unit comprising:
   a. an insulating band means with means to fasten said insulating band means close to a persons body;
   b. a replaceable strip fitting under said insulating band means;
   c. a chemical battery, an oxygen reference cell and multiple glucose sensing units formed on said replaceable strip;
   d. a wick means cooperating with said replaceable strip in said insulating band means to collect perspiration formed under said replaceable strip and to transport said perspiration past said oxygen reference cell and past said multiple glucose sensing units; said multiple glucose sensing units each comprising an oxygen measuring cell, an oxygen permeable membrane and fixed glucose oxidase membrane;

e. a group of carbon electrodes each immersed in a plateable solution with each one of said group of electrodes connected with circuitry to compare the difference in electrical output between said oxygen reference cell and said oxygen measuring cells in each of said glucose sensing units by plating individual ones of said group of carbon electrodes; said group of carbon electrodes and said circuitry being formed on said replaceable strip.

* * * * *